US010806367B2

United States Patent
Breeuwer et al.

(10) Patent No.: US 10,806,367 B2
(45) Date of Patent: Oct. 20, 2020

(54) SYSTEM AND METHOD FOR MYOCARDIAL PERFUSION PATHOLOGY CHARACTERIZATION (71) Applicants: KONINKLIJKE PHILIPS N.V., Eindhoven (NL); KINGS COLLEGE LONDON, London (GB)

(72) Inventors: Marcel Breeuwer, Eindhoven (NL); Amedeo Chiribiri, Eindhoven (NL); Eike Nagel, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1238 days.

(21) Appl. No.: 15/026,062

(22) PCT Filed: Oct. 1, 2014

(86) PCT No.: PCT/EP2014/071109
§ 371 (c)(1),
(2) Date: Mar. 30, 2016

(87) PCT Pub. No.: WO2015/049324
PCT Pub. Date: Apr. 9, 2015

(65) Prior Publication Data
US 2016/0235330 A1 Aug. 18, 2016

(30) Foreign Application Priority Data
Oct. 1, 2013 (EP) ..................................... 13186934

(51) Int. Cl.
A61B 5/00 (2006.01)
A61B 5/055 (2006.01)
(Continued)

(52) U.S. Cl.
CPC ............ *A61B 5/055* (2013.01); *A61B 5/0044* (2013.01); *A61B 5/026* (2013.01); *A61B 5/0402* (2013.01);
(Continued)

(58) Field of Classification Search
CPC ........ A61B 5/055; A61B 5/0044; A61B 5/025
See application file for complete search history.

(56) References Cited

U.S. PATENT DOCUMENTS

| 7,024,024 B1 | 4/2006 | Aiazian |
| 2003/0103670 A1* | 6/2003 | Schoelkopf ........... G06T 11/001 382/162 |

(Continued)

FOREIGN PATENT DOCUMENTS

| JP | 2010213760 A | 9/2010 |
| WO | 2005004066 A1 | 1/2005 |

(Continued)

OTHER PUBLICATIONS

Jerosch-Herold "Quantification of Myocardial Perfusion by Cariovascular Magneticresoance"Journal of Cardiovascular Magnetic Resonance, vol. 12, No. 1 Oct. 8, 2010.

(Continued)

*Primary Examiner* — Joseph M Santos Rodriguez (57) ABSTRACT

Characterizing myocardial perfusion pathology includes analyzing a plurality of medical images of at least a portion of the heart of a subject of interest (20), acquired in a consecutive manner by a medical imaging modality (10). Intensities of selected myocardial image positions from the plurality of medical images are sampled and assigned an index representing an order of acquisition to the respective sampled intensities of the myocardial image positions to obtain intensity curves (60). An index number (64, 66) indicative of a spatio-temporal perfusion inhomogeneity or (Continued)

perfusion dephasing among at least a subset of myocardial segments of the plurality of myocardial segments is calculated, based on the obtained intensity curves (60).

20 Claims, 4 Drawing Sheets

(51) Int. Cl.
  *A61B 6/03*    (2006.01)
  *A61B 6/00*    (2006.01)
  *A61B 8/06*    (2006.01)
  *A61B 8/08*    (2006.01)
  *A61B 5/026*    (2006.01)
  *G01R 33/563*    (2006.01)
  *G06T 7/00*    (2017.01)
  *A61B 5/04*    (2006.01)
  *A61B 5/0402*    (2006.01)
  *G01R 33/56*    (2006.01)

(52) U.S. Cl.
  CPC ......... *A61B 5/04017* (2013.01); *A61B 6/032* (2013.01); *A61B 6/037* (2013.01); *A61B 6/481* (2013.01); *A61B 6/503* (2013.01); *A61B 6/507* (2013.01); *A61B 8/06* (2013.01); *A61B 8/481* (2013.01); *G01R 33/56366* (2013.01); *G06T 7/0016* (2013.01); *A61B 8/0883* (2013.01); *G01R 33/5608* (2013.01); *G06T 2207/10076* (2013.01); *G06T 2207/30048* (2013.01); *G06T 2207/30104* (2013.01)

(56) References Cited

U.S. PATENT DOCUMENTS

| 2005/0065432 A1 | 3/2005 | Kimura | |
|---|---|---|---|
| 2006/0155185 A1* | 7/2006 | Breeuwer | A61B 5/055 600/407 |
| 2006/0173297 A1* | 8/2006 | Popescu | A61B 6/481 600/431 |
| 2007/0203412 A1 | 8/2007 | Sugiura | |
| 2010/0183207 A1 | 7/2010 | Sakaguchi et al. | |
| 2011/0285702 A1 | 11/2011 | Hautvast et al. | |

FOREIGN PATENT DOCUMENTS

| WO | 2010086771 A1 | 8/2010 |
|---|---|---|
| WO | 2010086810 A1 | 8/2010 |

OTHER PUBLICATIONS

Marcel Breeuwer Comprehensive Visualization of First Pass Myocardial Perfusion: The Uptake Movie and the Perfusogram) ISMRM 2002.

J. Downey, H. Downey, and E. Kirk, Effects of Myocardial Strains on Coronary Blood Flow, Circulation Research American Heart Association, 34(3):286-292, 1974.

J. Downey and E. Kirk, Distribution of the Coronary Blood Flow across the Canine Heart Wall during Systole, Circulation Research, 34(2):251-257, 1974.

J. Downey and E. Kirk, Inhibition of coronary blood flow by a vascular waterfall mechanism, Circulation Research, 36(6):753-760, 1975.

G. Path et al., Correlation between transmural high energy phosphate levels and myocardial blood flow in the presence of graded coronary stenosis, Circulation Research, 67(3):660-673, 1990.

M. Jerosch-Herold, Quantification of myocardial perfusion by cardiovascular magnetic resonance, Journal of Cardiovascular Magnetic Resonance, 12(1):57, 2010.

G.L.T.F. Hautvast et al., Quantitative Analysis of Transmural Gradients in Perfusion Cardiac Magnetic Resonance Images, Magnetic Resonance in Medicine, 2011.

J. Downey and E. Kirk, The Transmural Distribution of Coronary Blood Flow During Maximal Vasodilation, Proceedings of the Society for Experimental Biology and Medicine, 150(1):189-193, 1975.

J.T. Keijer et al., Magnetic resonance imaging of myocardial perfusion in single-vessel coronary artery disease: implications for transmural assessment of myocardial perfusion,Journal of Cardiovascular Magnetic Resonance: Official Journal of the Society forCardiovascular Magnetic Resonance, 2(3):189-200, 2000.

* cited by examiner

SYSTEM AND METHOD FOR MYOCARDIAL PERFUSION PATHOLOGY CHARACTERIZATION

CROSS REFERENCE TO RELATED APPLICATIONS

This application is a U.S. national phase application of International Application No. PCT/EP2014/071109, filed on Oct. 1, 2014, which claims the benefit of EP Application Serial No. 13186934.9 filed on Oct. 1, 2013 and is incorporated herein by reference.

FIELD OF THE INVENTION

The invention relates to the field of medical imaging of the heart, and in particular to the field of analyzing medical images of the heart.

BACKGROUND OF THE INVENTION

First-pass enhancement imaging of the heart by cardiac magnetic resonance (CMR) imaging, and more recently also cardiac computed tomography (CCT) imaging, allows for quantification of myocardial perfusion. This quantification includes semi-quantitative or true quantitative analysis of time-intensity curves. Semi-quantitative analysis comprises quantification of several characteristic features of time-intensity curves, for instance peak intensity, maximum upslope, mean transit time, and others. In true quantitative analysis, the actual myocardial blood flow is calculated from a mathematical analysis of the arterial input function (AIF) and the time-intensity curves obtained in the myocardium. An extensive review of both semi-quantitative and true quantitative approaches is given in Jerosch-Herold: Quantification of myocardial perfusion by cardiovascular magnetic resonance, Journal of Cardiovascular Magnetic Resonance 2010, 12:57.

Published US Patent Application No. 2006/0155185 to Breeuwer (see also International application WO 2005/004066 A1) describes a method for quantitative assessment of cardiac perfusion. The method includes dividing a myocardium that is depicted on a series of cardiac images into image segments comprising at least one image pixel and determining a cardiac perfusion parameter for each of the image segments. Further, at least one image segment with a normal perfusion parameter value is selected, and subsequently, cardiac perfusion parameters of the remaining image segments are based on the normal perfusion parameter value. In one embodiment, the perfusion parameter is a maximum upslope of a time-intensity profile for distribution of a contrast agent in the myocardium. A normal maximum upslope is derived for at least one image segment and a relative maximum upslope is calculated for each segment with relation to the normal maximum upslope. Based on these values, a ratio of myocardial perfusion parameters derived at stress and myocardial perfusion parameters derived at rest is calculated for each segment. As an example, it is described to calculate a myocardial perfusion reserve index (MPRI) for each segment, defined as a ratio of the relative maximum upslopes derived at rest and at stress.

SUMMARY OF THE INVENTION

At present, myocardial perfusion deficits exist that require an application of invasive methods for characterization and analysis. Non-invasive imaging methods cannot reliably differentiate reliably between coronary microvascular dysfunction (MVD) and multi-vessel coronary artery disease (including left main coronary artery disease; CAD) as both these conditions may result in diffuse myocardial ischemia, which on visual and quantitative analysis can have a similar appearance. Consequently, patients are subjected to invasive angiography, and coronary microvascular dysfunction is diagnosed after demonstrating normal coronary arteries in patients with myocardial ischemia.

Analysis of first-pass enhancement images may result in true quantification of the myocardial blood flow. While perfusion deficits can be analyzed by true quantification of the myocardial blood flow, non-invasive methods can, however, only assess the distribution and severity of ischaemia, but they cannot measure the spatio-temporal homogeneity of perfusion in different segments of the myocardium. For instance, MVD and CAD are both characterized by a severe and spatially widespread ischaemia, usually associated with a delayed arrival of contrast agent to the endocardial layers of the myocardium.

It is therefore an object of the invention to provide an improved method of characterizing myocardial perfusion pathology by analyzing a plurality of medical images of at least a portion of the heart of a subject of interest, the plurality of medical images being acquired in a consecutive manner by a medical imaging modality.

This object is achieved by the method comprising the following steps:

delineating contours of a selected part of the heart of the subject of interest in the plurality of medical images and segmenting the selected part into a plurality of segments;

sampling intensities of selected myocardial image positions from the plurality of medical images and assigning an index representing an order of acquisition of each one of the medical images to the respective sampled intensities of the myocardial image positions to obtain intensity curves for each of the selected myocardial image positions;

calculating an index number indicative of a spatio-temporal perfusion inhomogeneity or perfusion dephasing among at least a subset of myocardial segments of the plurality of myocardial segments, based on the obtained intensity curves.

The phrase "a selected part of the heart", as used in this application, shall be understood particularly as any vascular cavity of the heart, and shall also be understood to encompass the left ventricle and the ascending aorta.

The phrase "medical imaging modality", as used in this application, shall particularly encompass cardiac magnetic resonance (CMR) imaging devices, cardiac computed tomography (CCT) imaging devices, coronary angiography (CA) devices, CCT angiography (CCTA) devices, intravascular ultrasound (IVUS) devices, single-photon emission computed tomography (SPECT) devices, positron emission tomography (PET) devices and echocardiography devices.

The phrase "spatio-temporal perfusion inhomogeneity" may also be referred to as "spatial-temporal dephasing" in this application, and shall be understood particularly as the temporal and spatial distribution of inhomogeneous myocardial blood flow in case of a pathologic abnormality.

The step of delineating contours of the selected part of the heart may be carried out manually, semi-automatically or fully automatically. Appropriate segmentation techniques are known in the art, commercially available and shall therefore not be discussed in more detail herein.

The subset of myocardial segments may comprise a strict subset of the plurality of myocardial segments like a perfusion territory, or it may comprise the complete myocardium.

The index representing an order of acquisition of each one of medical images may be referenced to a timescale, and may be time itself.

One advantage of the method lies in the fact that additional temporal information is provided on the distribution of perfusion to different regions of the selected part of the heart that can be used to characterize specific myocardial pathologies in a fast and simple way. In particular, the calculated index number can be used to distinguish coronary artery disease and microvascular disease in a characterization.

Another advantage of the method is that the additional information can be provided by a non-invasive method, so that an invasive angiographic assessment can be avoided in many cases.

Prior to applying the step of delineating contours of the selected part of the heart, the plurality of medical images may have been subjected to an image registration technique to correct for breathing motion of the subject of interest. Appropriate registration techniques are well known in the art and shall therefore not be discussed in detail herein.

Further, the obtained curves of intensity may have been subjected to filtering for better result. Any filtering technique that is suitable to the person skilled in the art may be employed.

In a preferred embodiment, the method further comprises a step of conducting quantification of myocardial blood flow in each segment of the plurality of segments. The step of conducting true quantification of myocardial blood flow may be carried out according to one of the state-of-the-art techniques described in the review article presented in the Background section, as for instance a deconvolution method, or according to any other technique that the person skilled in the art considers to be suitable. The true quantification of myocardial blood flow in each segment can provide complementary information for characterizing myocardial perfusion pathology.

In another embodiment of the method, the plurality of medical images is acquired by the medical imaging modality after administering a contrast agent to the subject of interest. The phrase "contrast agent", as used in this application, shall be understood particularly as any agent that generates a larger signal compared to a baseline when being acquired by the medical imaging modality than the tissue of the subject of interest surrounding the agent. If the medical imaging modality is based on a working principle using gamma rays, the phrase "contrast agent" shall also encompass radioactive tracer materials. In this way, a signal-to-noise ratio can be improved and a more exact characterization of myocardial fusion pathology can be accomplished.

In one embodiment, the plurality of medical images may be acquired after administering the contrast agent to the subject of interest and during first-pass of the contrast agent through the heart.

In another embodiment, the plurality of medical images may be acquired after administering the contrast agent to the subject of interest, and during a time when a concentration of the contrast agent has reached a steady-state concentration in the subject of interest. This is of special importance for acquiring medical images by stress echo perfusion imaging.

In one embodiment, the plurality of medical images may be acquired using endogenous contrast, like e.g. arterial spin labeling, and during first-pass of the contrast agent through the heart.

In another preferred embodiment, the method further comprises a step of identifying a reference location in the selected part of the heart, wherein in the step of calculating the index number, the intensity curves are evaluated with reference to a reference time that is determined by the identified reference location. By that, a precise reference for calculating the index number can be provided. A preferred reference location is the left ventricle, as the left ventricle is the location that receives the contrast agent during first-pass and precedes the upslope in the obtained intensity curves for each of the selected myocardial image positions. The phrase "upslope", as used in this application, shall be understood particularly as a moment in time when an intensity of the obtained intensity curves due to the administering of the contrast agent exceeds a predetermined threshold, e.g. of 10%, compared to an intensity without the contrast agent.

In another preferred embodiment, the method further comprises a step of automatically determining, for each of the selected myocardial positions, an individual time period relative to a reference time that is determined by the identified reference location until an occurrence of a characteristic feature of the sampled intensity of each of the myocardial image positions. Then, the individual time periods are used in the step of calculating the index number. The characteristic feature may be a point in time of onset of intensity rise, a point in time of peak intensity, or any other characteristic feature that appear suitable to the person skilled in the art. In this way, the index number indicative of the spatio-temporal perfusion inhomogeneity can readily be calculated in an automatic way.

Preferably, the step of calculating the index numbers comprises a calculation of a statistical measure that is indicative of a variation of the time until occurrence of the characteristic feature at each of the individual myocardial positions relative to the time of occurrence of the characteristic feature at the identified reference location. By that, an index number can be provided that describes the spatio-temporal perfusion inhomogeneity among the myocardial segments in a very significant way. The statistical measure may have the form of the variance, customarily used in statistics as a measure of how far a set of numbers spreads out. In this sense, the variance may be the square of the standard deviation of the set of numbers. In general, the statistical measure may have any other form that the person skilled in the art considers suitable for indicating the variation of the time until occurrence of the characteristic feature at each of the individual myocardial positions.

Preferably, the acquiring of the plurality of medical images of at least a portion of the heart of the subject of interest is at least partially synchronized to a cyclic movement of the heart of the subject of interest. For instance, a medical image can be acquired at a fixed amount of time before or after a reference event in the electrocardiogram like the R-peak of the QRS complex. An advantage of this embodiment of the method is that all medical images of the plurality of medical images are taken at a similar status of the heart, so that there is little motion of the myocardial ventricle among the medical images, and the myocardium is rendered relatively stationary.

In yet another embodiment of the method, in the step of sampling intensities of myocardial image positions, the myocardial image positions are selected in a direction along the myocardium as well as in a direction across the myocardium. In this way, the calculated index number represents the spatio-temporal perfusion inhomogeneity among the myocardial segments in an especially proper way.

The method may further comprise a step of generating a perfusogram and displaying it to a user. The phrase "perfusogram", as used in this application, shall be understood particularly as a color representation of the intensities of image positions in the myocardium as a function of position and time. The horizontal axis of the perfusogram may represent time and the vertical axis may represent position (i.e. segment) in the myocardium. "Perfusograms" has been described as a useful tool of visualizing myocardial perfusion in publications earlier, for instance in: Marcel Breeuwer, Comprehensive visualization of first-pass myocardial perfusion: The uptake movie and the perfusogram", (International Society for Magnetic Resonance in Medicine) ISMRM 2002. For instance, the perfusogram may be displayed on a monitor unit that is customary for the medical imaging modality the plurality of medical images has been acquired with.

Furthermore, the method may preferably comprise a step of implementing at least one marker in the perfusogram that is indicative of at least one characteristic position and/or at least one characteristic point in time. Examples of such markers that can convey information contained in the perfusogram in a fast way to the user are positions of the coronary artery perfusion territories, borders of the segments of the left ventricle (for instance, according to the AHA 17 segment model) and characteristic moments in time of the passage of the contrast agent like time of onset and time of peak. The marker may be formed as a straight line, a curved line, or as a closed loop marking a territory of the myocardium.

In another preferred embodiment, the method may further comprise a step of implementing a plurality of computer links, wherein each computer link of the plurality of computer links is assigned to a location in the perfusogram, and wherein each computer link of the plurality of computer links is linked to a data set representing a medical image of the plurality of medical images. In this way, detailed information on the myocardial blood flow can be readily provided to the user, usually a medical staff member.

It is another object of the invention to provide a system for myocardial perfusion pathology characterization by analyzing a plurality of medical images of at least a portion of the heart of a subject of interest. The plurality of medical images is acquired in a consecutive manner by a medical imaging modality. The system comprises a delineation unit, provided for delineating contours of a selected part of the heart of the subject of interest in the plurality of medical images and for segmenting the selected part into a plurality of segments, and an intensity sampler and analyzing unit.

The intensity sampler and analyzing unit is configured for sampling intensities of myocardial image positions from the plurality of medical images and assigning an index representing an order of acquisition of each one of the medical images to the respective sampled intensities of the myocardial image positions, and for calculating an index number indicative of a spatio-temporal perfusion inhomogeneity or perfusion dephasing among at least a subset of myocardial segments of the plurality of myocardial segments. The system can provide the same advantages as disclosed above for the method.

In another aspect of the invention, the system for myocardial perfusion pathology characterization is an integral part of the medical imaging modality that the plurality of medical images has been acquired with. Preferably, the medical image modality is designed as a magnetic resonance imaging apparatus. The magnetic resonance imaging apparatus may advantageously comprise synchronization means for synchronizing an acquiring of medical images to a cyclic movement of the heart of the subject of interest.

In yet another aspect of the present invention, a software module is provided for carrying out an embodiment of any of the methods of characterizing myocardial perfusion pathology disclosed above or a combination thereof, wherein the method steps to be conducted are converted into a program code of the software module, wherein the program code is implementable in a memory unit of a control unit of the medical imaging modality and is executable by a processor unit of the control unit of the medical imaging modality.

The control unit may be the control unit that is customary for controlling functions of the medical imaging modality. The control unit may alternatively be an additional control unit that is especially assigned to execute the method steps.

The software module can enable a robust and reliable execution of the method and can allow for a fast modification of method steps and/or an adaptation of the image registration algorithm.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

Figure 1:
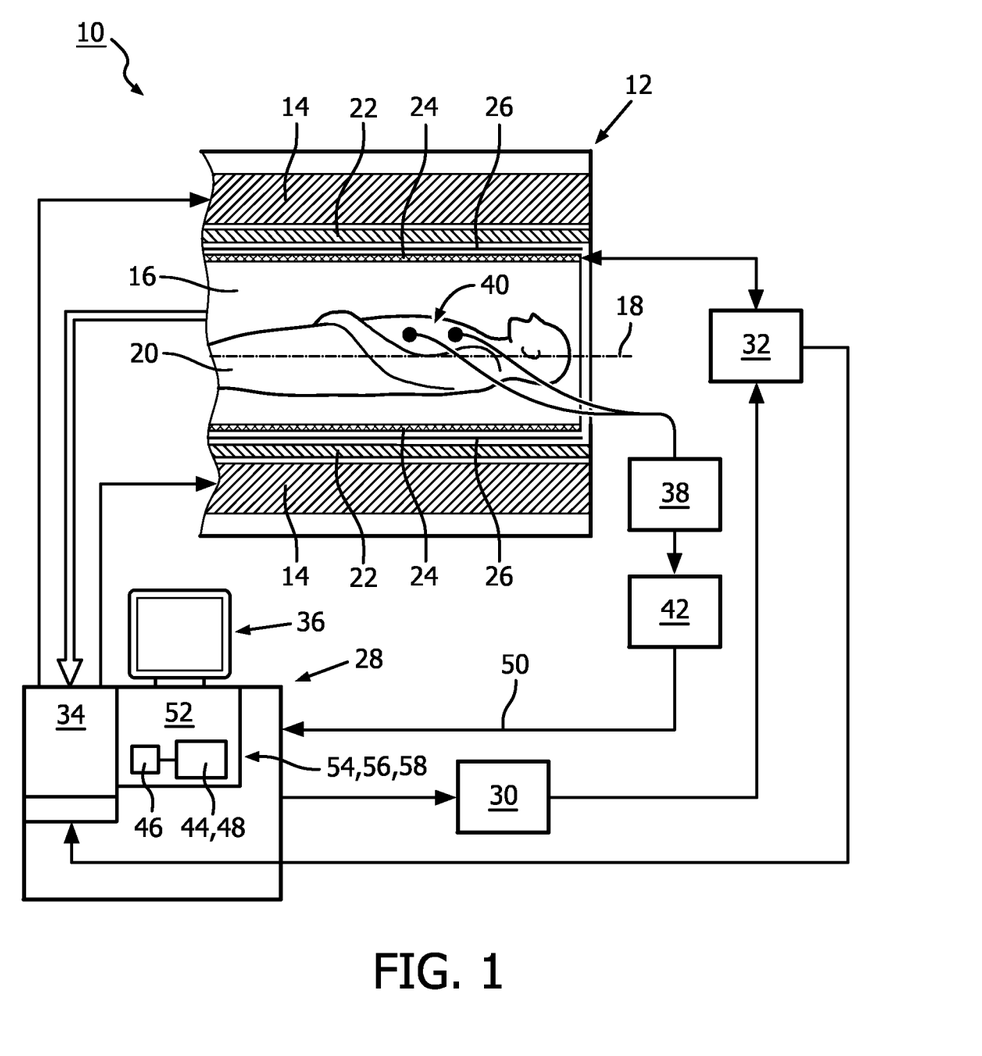
FIG. 1 is a schematic illustration of a part of an embodiment of a medical imaging modality in accordance with the invention, designed as a magnetic resonance imaging system.

FIG. 1 shows a schematic illustration of a part of an embodiment of a medical imaging modality 10 in accordance with the invention that is designed as a magnetic resonance imaging system, for acquisition of medical images, represented by magnetic resonance images, of at least a portion of the heart of a human subject of interest 20. The magnetic resonance imaging system comprises a magnetic resonance scanner 12 having a main magnet 14 provided for generating a static magnetic field. The main magnet 14 has a central bore that provides an examination space 16 around a center axis 18 for the subject of interest 20 to be positioned within. For clarity reasons, a conventional table for supporting the subject of interest 20 has been omitted in FIG. 1. The substantially static magnetic field defines an axial direction of the examination space 16, aligned in parallel to the center axis 18. Further, the magnetic resonance imaging system 10 includes a magnetic gradient coil system 22 provided for generating gradient magnetic fields superimposed to the static magnetic field. The magnetic gradient coil system 22 is concentrically arranged within the bore of the main magnet 14, as is known in the art.

In principle, the invention is also applicable to any other type of magnetic resonance imaging system providing an examination region within a static magnetic field. Furthermore, it is appreciated that the invention can be used with any other medical imaging modality that is configured to acquire medical images of at least a portion of the heart of the subject of interest. Examples of medical imaging modalities that the invention can be applied to are cardiac computed tomography (CCT) imaging devices, coronary angiography (CA) devices, CCT angiography (CCTA) devices, intravascular ultrasound (IVUS) devices, single-photon emission computed tomography (SPECT) devices, positron emission tomography (PET) devices and echocardiography devices.

Further, the magnetic resonance imaging system comprises a radio frequency antenna designed as a whole-body coil 24 that is provided for applying a radio frequency electromagnetic field to the examination space 16 during radio frequency transmit phases to excite nuclei of or within the subject of interest 20. The whole-body coil 24 is also provided to receive magnetic resonance signals from the excited nuclei of or within the subject of interest 20 during radio frequency receive phases. In an operational state of the magnetic resonance imaging system, radio frequency transmit phases and radio frequency receive phases are taking place in a consecutive manner. The whole-body coil 24 has a center axis and, in the operational state, is arranged concentrically within the bore of the main magnet 14 such that the center axis of the whole-body coil 24 and the center axis 18 of the magnetic resonance imaging system coincide. As is well known in the art, a cylindrical metal radio frequency shield 26 is arranged concentrically between the magnetic gradient coil system 22 and the whole-body coil 24.

The magnetic resonance imaging system further includes a control unit 28 provided for at least controlling functions of the magnetic resonance scanner 12 and the magnetic gradient coil system 22. The control unit 28 comprises a customary monitor unit 36.

Furthermore, the magnetic resonance imaging system comprises a radio frequency transmitter unit 30 that is connected to and controlled by the control unit 28. The radio frequency transmitter unit 30 is provided to feed radio frequency power of a magnetic resonance radio frequency to the whole-body coil 24 via a radio frequency switching unit 32 during the radio frequency transmit phases. During radio frequency receive phases, the radio frequency switching unit 32 directs the magnetic resonance signals from the whole-body coil 24 to an image processing unit 36 residing in the control unit 28. The image processing unit 34 is configured for processing acquired magnetic resonance signals to generate a magnetic resonance image of the portion of the subject of interest 20 from the acquired magnetic resonance signals. Many different variations of this technique are well known to the person skilled in the art, and thus need not be described in further detail herein.

For the acquisition of magnetic resonance images of the heart of the subject of interest 20, the magnetic resonance imaging system comprises synchronization means for synchronizing an acquiring of medical images to a cyclic movement of the heart of the subject of interest. The synchronization means are formed as an electrocardiogram device 38 and a synchronization unit 42.

The electrocardiogram device 38 is provided for taking measurements of the electrocardiogram data of the heart of the subject of interest 20. To this end, a plurality of electrodes 40 of the electrocardiogram device 38 may be arranged at the subject of interest 20. Further, the electrocardiogram device 38 includes means for filtering the electrocardiogram data to reduce artifacts generated by magnetic gradient fields. Suitable filtering means are known to the person skilled in the art and shall therefore not be described in more detail herein.

The electrocardiogram device 38 is coupled to the synchronization unit 42, which is configured for generating a trigger signal 50 to trigger an acquisition period of acquiring magnetic resonance signals from a detection of the R-peak of the QRS complex of the heart activity. The synchronization unit 42, in turn, is coupled to the control unit 28. The control unit 28 is configured to be synchronized by the trigger signals 50 that are provided by the synchronization unit 42 for a generation of control signals for the magnetic gradient coil system 22 generating the gradient magnetic fields. To this end, the control unit 28 is configured to generate a plurality of sequences upon receiving the trigger signals 50, each sequence comprising radio frequency fields and magnetic gradient fields.

The medical imaging modality 10 comprises a system for myocardial perfusion pathology characterization 52 by analyzing a plurality of medical images of at least a portion of the heart of a subject of interest 20. The system for myocardial perfusion pathology characterization 52 resides within a housing of the control unit 28 and comprises a delineation unit 54, a blood flow analyzer 56 and an intensity sampler and analyzing unit 58. The functions and interactions of these devices will be explained in detail thereinafter.

In a consecutive manner, a plurality of medical images in the form of magnetic resonance images of the heart of the subject of interest 20 is acquired by the magnetic resonance imaging system after administering a contrast agent to the subject of interest 20 during first-pass of the contrast agent through the heart of the subject of interest 20. A plurality of medical images has been acquired for three different subjects of interest: a control individual, an individual with a three-vessel coronary artery disease, and an individual having a microvascular dysfunction, respectively. The acquiring of the plurality of medical images of the heart of the subject of interest 20 has been synchronized to the cyclic movement of the respective heart of the subject of interest 20 as described above.

After the acquiring of each plurality of medical images of the heart of the respective subject of interest 20, the medical images are analyzed by an embodiment of a method of characterizing myocardial perfusion pathology in accordance with the invention. The method is described in detail in the following as being applied to one plurality of medical images. It is understood that the method is applied in the same way also to the other two pluralities of medical images.

In order to be able to carry out the method, the system for myocardial perfusion pathology characterization 52 comprises a software module 48 (FIG. 1). The method steps to be conducted are converted into a program code of the software module 48, wherein the program code is implementable in a memory unit 44 of the system for myocardial perfusion pathology characterization 52 and is executable by a processor unit 46 of the system for myocardial perfusion pathology characterization 52.

In a preparatory step, each medical image of the plurality of medical images is submitted to an image registration algorithm.

In the first step of the method, contours of the left ventricle of the heart of the subject of interest 20 are delineated in the plurality of medical images and the left ventricle is segmented into a plurality of segments by the delineation unit 54 of the system for myocardial perfusion pathology characterization 52.

In the next step of the method, the blood flow analyzer 56 of the system for myocardial perfusion pathology characterization 52 conducts a true quantification of myocardial blood flow in each segment of the plurality of segments.

Then, myocardial image positions are selected by the intensity sampler and analyzing unit 58 of the system for myocardial perfusion pathology characterization 52. The myocardial image positions are selected in a direction along the myocardium as well as in a direction across the myocardium. The intensity sampler and analyzing unit 58 then samples intensities of the selected myocardial image positions from the plurality of medical images and assigns an index representing an order of acquisition formed by a time of acquisition of each one of the medical images to the respective sampled intensities of the myocardial image positions to obtain intensity curves 60 over time for each of the selected myocardial image positions.

Figure 2:
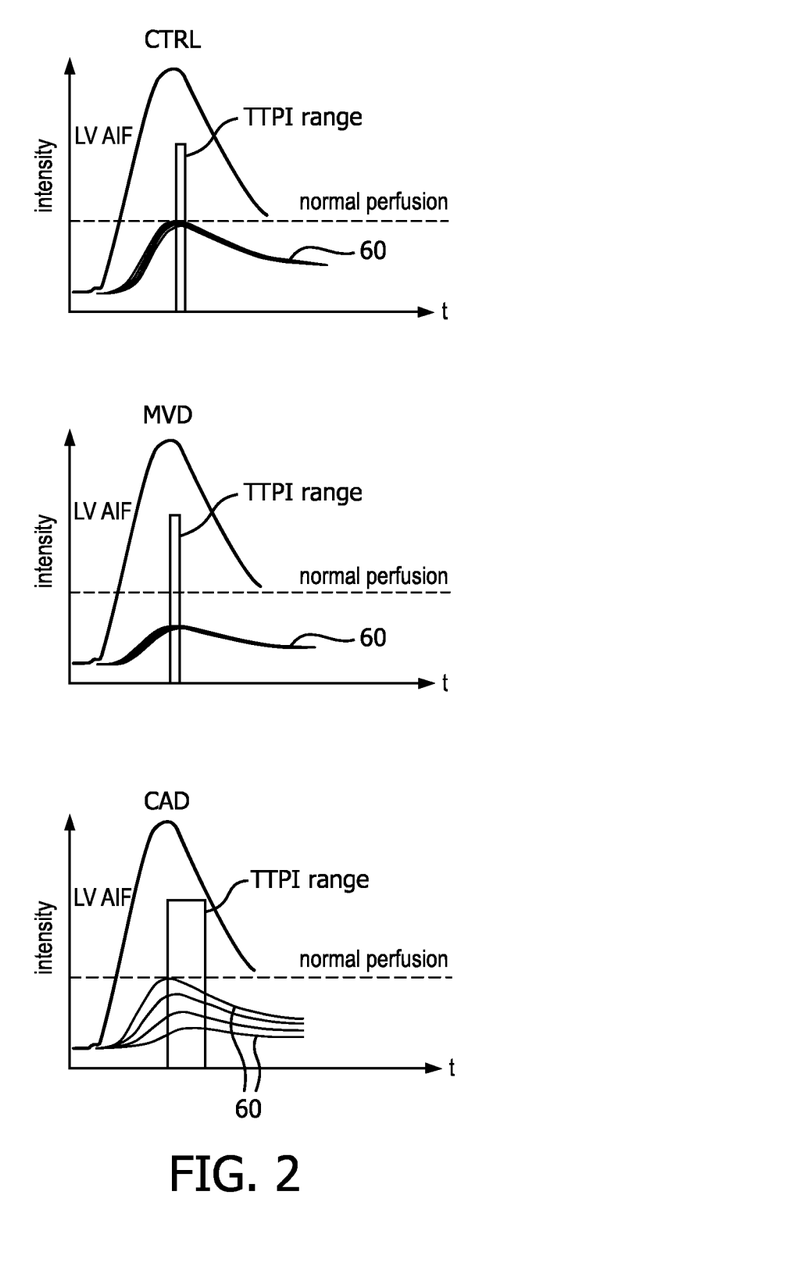
FIG. 2 is a schematic illustration of intensity curves obtained in accordance with the invention for myocardial perfusion during first-pass of a contrast agent through the heart of the control individual (top), through the heart of an individual having a microvascular dysfunction (middle), and through the heart of an individual with a three-vessel coronary artery disease (bottom)

The obtained intensity curves 60 over time for the three different subject of interest are schematically shown in FIG. 2 (top: control individual, middle: individual having a microvascular dysfunction (MVD), bottom: individual with a three vessel coronary artery disease (CAD)).

For the intensity curves 60 over time in FIG. 2, in order to provide for a suitable timescale, a reference location in the left ventricle was identified by the intensity sampler and analyzing unit 58. The reference location is a location first to receive the contrast agent during first-pass of the contrast agent and precedes an onset of rise of the intensities of the selected myocardial image positions. The point in time of the onset of rise of the intensity at the reference location serves as a reference time. The intensity curves 60 over time are evaluated with reference to the identified reference location and reference time.

In a next step of the method, for each of the selected myocardial positions an individual time period relative to the identified reference location and corresponding reference time is automatically determined until an occurrence of a characteristic feature in the sampled intensity curve 60 of each of the myocardial image positions. In this embodiment, the characteristic feature is a peak intensity of the intensity curve over time. The individual time periods to peak intensity TTPI are used in a next step of calculating an index number 64, 66.

In a following step of the method, the intensity sampler and analyzing unit 58 calculates a first index number 64 which is indicative of a spatio-temporal perfusion inhomogeneity or dephasing among a subset of myocardial segments of the plurality of myocardial segments, based on the obtained intensity curves 60 over time.

The first index number 64 indicative of the temporal dephasing of the left ventricular perfusion is calculated in a next step as a variance of the time periods to peak intensity TTPI between the reference time and the time until the occurrence of the peak intensity of the intensity curves 60 over time. Herein, the variance is understood to be the square of the standard deviation of the time periods TTPI.

A second index number 66 indicative of the temporal dephasing of the left ventricular perfusion is calculated as a coefficient of variation of the time periods to peak intensity TTPI between the reference time and the time until the occurrence of the peak intensity of the intensity curves 60 over time.

Figure 3:
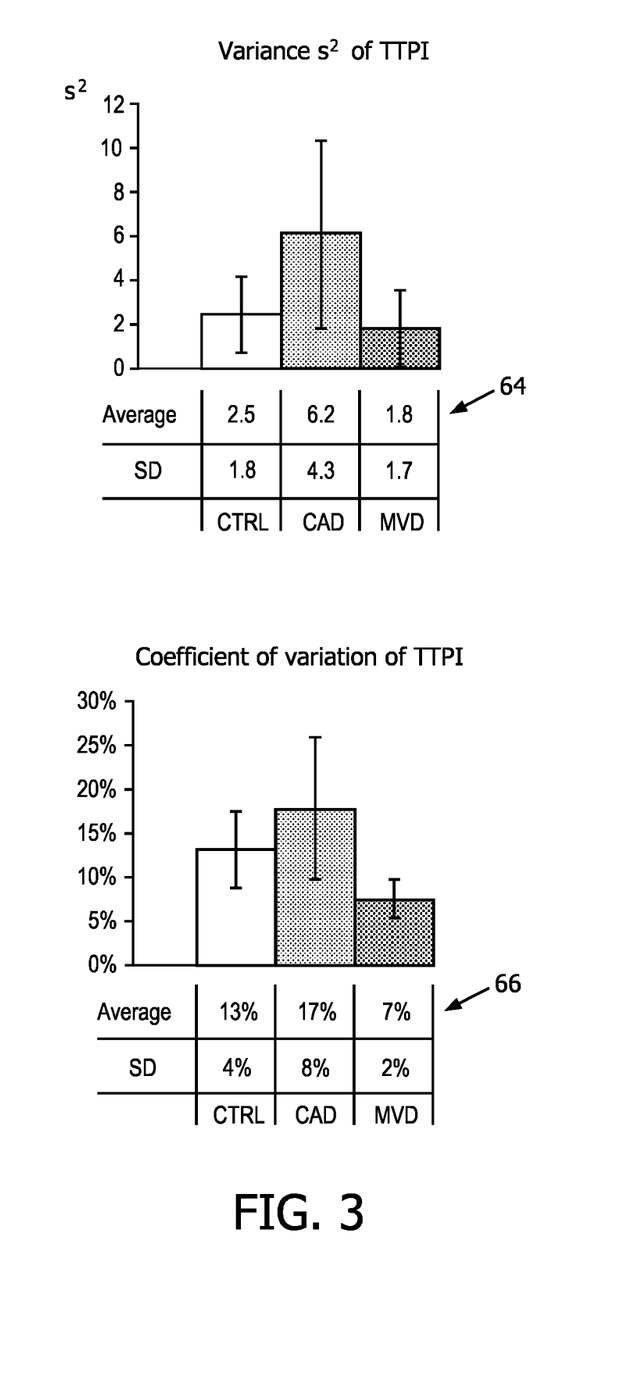
FIG. 3 shows diagrams comprising calculated index numbers indicative of spatio-temporal perfusion inhomogeneity, calculated from the intensity curves pursuant to FIG. 2.

The results for the calculated index number 64, 66 displayed in FIG. 3 clearly show significant differences between the control individual (CTRL, left column), the individual with a three vessel coronary artery disease (CAD, center column), and the one having a microvascular dysfunction (MVD, right column).

As becomes apparent from the intensity curves 60 over time in FIG. 2, MVD and three-vessel CAD are both characterized by a severe and spatially widespread ischaemia, usually associated with a delayed arrival of contrast agent to the endocardial layers of the myocardium. However, adding spatio-temporal dephasing analysis can provide additional information on the temporal distribution of perfusion to different regions of the left ventricle. FIG. 3 shows that the calculated index number 64, 66 constitutes the main difference between CAD and MVD due to the different underlying pathophysiology and allows for a specific characterization.

In the individual with CAD, the spatio-temporal distribution of myocardial blood flow in the myocardium is increasingly inhomogeneous. In the individual with MVD instead, the pathologic alteration involves the microscopic circulation and its interaction in systole with myocardial contraction. In this case, perfusion to the epicardial layer is unobstructed and very homogeneous. However, there is a delay in the transmural propagation of the first-pass wave. Similarly to CAD, this causes widespread ischaemia with delayed intensity rise onset. However, this feature is homogeneous in the temporal domain throughout the myocardium, allowing the non-invasive differentiation between CAD and MVD.

Figure 4:
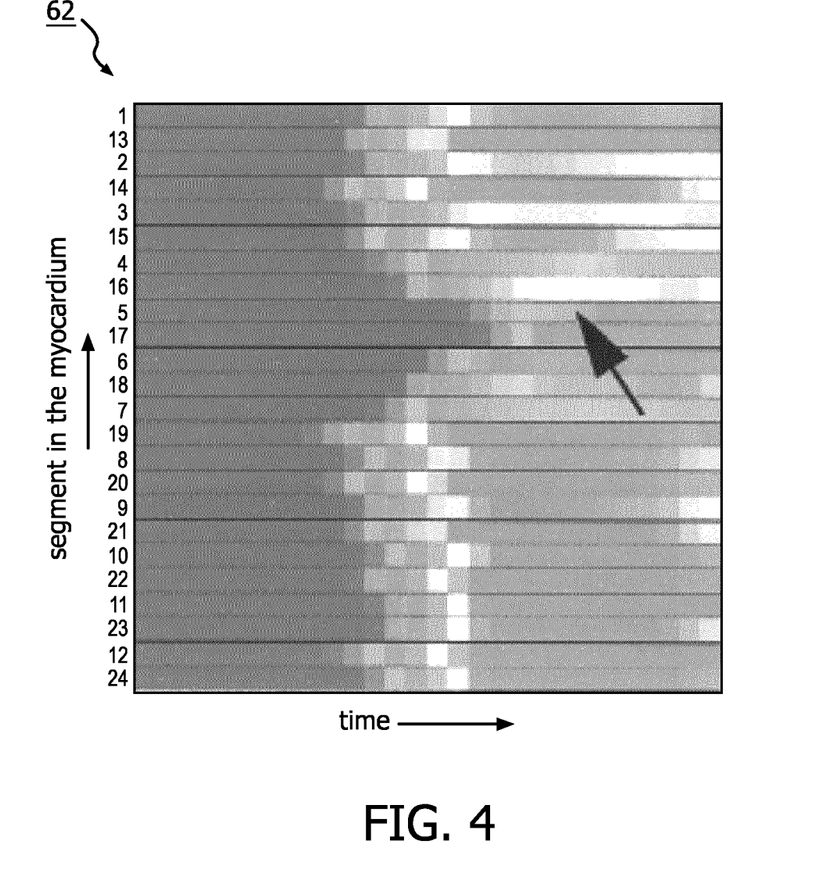
FIG. 4 illustrates an example of a perfusogram.

In another step of the method, a perfusogram 62 is generated and displayed to a user by the monitor unit 36. FIG. 4 illustrates an example of a perfusogram 62 having a gray-scale or color-coding. Markers like straight lines can be implemented in the perfusogram 62 (not shown) that are indicative of characteristic positions and/or characteristic points in time. Other markers can be inserted in the perfusogram 62 as well (not shown) that are formed as closed loops, and that are indicative of a regime of time and space in which the myocardium is less well perfused.

In yet another step of the method, a plurality of computer links is implemented in the perfusogram 62. Each computer link of the plurality of computer links is assigned to a location in the perfusogram 62, and each computer link of the plurality of computer links is linked to a data set representing a medical image of the plurality of medical images The computer mouse cursor shown in FIG. 4 is pointing at a location of the perfusogram 62 that represents a specific point in time and a specific location in the myocardium. By clicking a mouse button, the computer link to the data set representing the medical image corresponding to the point in time and location of the myocardium is activated, and the medical image is displayed on the monitor unit 36 of the magnetic resonance imaging system.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

REFERENCE SYMBOL LIST 10 medical imaging modality
12 magnetic resonance scanner 14 main magnet
16 examination space
18 center axis
20 subject of interest
22 magnetic gradient coil system
24 whole-body coil
26 radio frequency shield
28 control unit
30 radio frequency transmitter unit
32 radio frequency switching unit
34 image processing unit
36 monitor unit
38 electrocardiogram device
40 electrode
42 synchronization unit
44 memory unit
46 processor unit
48 software module
50 trigger signal
52 system for myocardial perfusion pathology characterization
54 delineation unit
56 blood flow analyzer
58 intensity sampler and analyzing unit
60 intensity curve over time
62 perfusogram
64 first index number
66 second index number
AIF arterial input function
LV left ventricle
TTPI time to peak intensity

The invention claimed is:

1. A method of characterizing myocardial perfusion pathology by analyzing a plurality of medical images of at least a portion of the heart of a subject of interest, the plurality of medical images being acquired in a consecutive manner by a medical imaging modality, the method comprising:
   segmenting a selected part of the heart of the subject of interest in the plurality of medical images into a plurality of segments;
   sampling intensities attributable to myocardial blood flow in selected myocardial image positions from the plurality of medical images and assigning an index representing an order of acquisition of each one of the medical images to the respective sampled intensities of the myocardial image positions to obtain intensity curves for each of the selected myocardial image positions;
   calculating an index number indicative of a spatio-temporal perfusion inhomogeneity or perfusion dephasing among at least a subset of myocardial segments of the plurality of myocardial segments, wherein the subset of myocardial segments includes a plurality of myocardial segments, based on the obtained intensity curves;
   based on the calculated index number, differentiating between coronary microvascular dysfunction (MVD) and coronary artery disease (CAD).

2. The method as claimed in claim 1, further comprising a step of
   quantifying the myocardial blood flow in each segment of the plurality of segments.

3. The method as claimed in claim 1, wherein the plurality of medical images is acquired by the medical imaging modality after administering a contrast agent to the subject of interest.

4. The method as claimed in claim 1, further comprising:
   identifying a reference location in the selected part of the heart, wherein calculating the index number includes evaluating with reference to a reference time that is determined by the identified reference location.

5. The method as claimed in claim 4, wherein the step of calculating the index number comprises a calculation of a statistical measure that is indicative of a variation of an individual time period (TTPI) relative to a reference time until the characteristic intensity is sampled at each of the individual myocardial positions relative to the time of occurrence of the characteristic feature at the identified reference location.

6. The method as claimed in claim 1, wherein the acquiring of the plurality of medical images of at least a portion of the heart of the subject of interest is at least partially synchronized to a cyclic movement of the heart of the subject of interest.

7. The method as claimed in claim 1, wherein in the step of sampling intensities of myocardial image positions, the myocardial image positions are selected in a direction along the myocardium as well as in a direction across the myocardium.

8. The method as claimed in claim 1, further comprising a step of generating a perfusogram and displaying it to a user.

9. The method as claimed claim 8, further comprising a step of implementing at least one marker in the perfusogram that is indicative of at least one characteristic position and/or at least one characteristic point in time.

10. A non-transitory computer-readable medium carrying software that controls a computer processor to perform the method as claimed in claim 1.

11. A system for myocardial perfusion pathology characterization by analyzing a plurality of medical images of at least a portion of a heart of a subject of interest, the plurality of medical images being acquired in a consecutive manner by a medical imaging modality, the system comprising:
   a computer processor configured to perform the method as claimed in claim 1.

12. A method of characterizing myocardial perfusion pathology by analyzing a plurality of medical images of at least a portion of the heart of a subject of interest, the plurality of medical images being acquired in a consecutive manner by a medical imaging modality, the method comprising:
   segmenting a selected part of the heart of the subject of interest in the plurality of medical images into a plurality of segments;
   sampling intensities attributable to myocardial blood flow in selected myocardial image positions from the plurality of medical images and assigning an index representing an order of acquisition of each one of the medical images to the respective sampled intensities of the myocardial image positions to obtain intensity curves for each of the selected myocardial image positions;
   calculating an index number indicative of a spatio-temporal perfusion inhomogeneity or perfusion dephasing among at least a subset of myocardial segments of the plurality of myocardial segments, wherein the subset of myocardial segments includes a plurality of myocardial segments, based on the obtained intensity curves;
   identifying a reference location in the selected part of the heart, wherein in the step of calculating the index number, the intensity curves are evaluated with reference to a reference time that is determined by the identified reference location; and automatically determining, for each of the selected myocardial positions, an individual time period (TTPI) relative to a reference time that is determined by the identified reference location, until a characteristic intensity is sampled of each of the myocardial image positions, wherein the individual time periods (TTPI) are used in the step of calculating the index number.

13. The method as claimed in claim 12, further comprising:
quantifying the myocardial blood flow in each segment of the plurality of segments.

14. The method as claimed in claim 12, wherein the plurality of medical images is acquired by the medical imaging modality after administering a contrast agent to the subject of interest.

15. The method as claimed in claim 12, wherein the acquiring of the plurality of medical images of at least a portion of the heart of the subject of interest is at least partially synchronized to a cyclic movement of the heart of the subject of interest.

16. A system for myocardial perfusion pathology characterization by analyzing a plurality of medical images of at least a portion of the heart of a subject of interest, the plurality of medical images being acquired in a consecutive manner by a medical imaging modality, the system comprising:
one or more processors configured to:
segment a selected part of the heart of the subject of interest in the plurality of medical images into a plurality of segments;
sample intensities indicative of myocardial blood flow in myocardial image positions from the plurality of medical images,
assign an index representing an order of acquisition of each one of the medical images to the respective sampled intensities of the myocardial image positions, and
calculate an index number indicative of a spatio-temporal perfusion inhomogeneity or perfusion dephasing among at least a subset of myocardial segments of the plurality of myocardial segments, wherein calculating the index number includes determining a reference time and calculating a statistical measure indicative of variation of individual time period (TTPI) from the reference time until a characteristic intensity occurs at each of the individual myocardial positions.

17. The system as claimed in claim 16, further including a magnetic resonance imaging apparatus configured to generate the plurality of medical images.

18. The system as claimed in claim 16, wherein the one or more processors are further configured to generate a perfusogram and further including:
a display configured to display the perfusogram.

19. The system as claimed in claim 16, wherein the one or more processors are further configured to quantify the myocardial blood flow in each of the plurality of segments.

20. The system as claimed in claim 16, wherein the plurality of medical images are contrast agent enhanced and synchronized to cyclic heart motion.

* * * * *